(12) United States Patent
Pelerin

(10) Patent No.: US 6,572,374 B2
(45) Date of Patent: Jun. 3, 2003

(54) DENTAL BONDING FORMULATION COMPLEXING CALCIFIED DEPOSITS ASSOCIATED WITH A DENTINAL TUBULE OPENING

(75) Inventor: Joseph J. Pelerin, Clarkston, MI (US)

(73) Assignee: Advantage Dental Products, Inc., Lake Orion, MI (US)

( * ) Notice: Subject to any disclaimer, the term of this patent is extended or adjusted under 35 U.S.C. 154(b) by 0 days.

(21) Appl. No.: 09/880,477

(22) Filed: Jun. 13, 2001

(65) Prior Publication Data

US 2002/0009693 A1 Jan. 24, 2002

Related U.S. Application Data

(60) Provisional application No. 60/211,359, filed on Jun. 13, 2000.

(51) Int. Cl.⁷ .................................................. A61C 5/02
(52) U.S. Cl. ..................................... 433/224; 433/228.1
(58) Field of Search ............................... 433/224, 226, 433/228.1; 523/116

(56) References Cited

U.S. PATENT DOCUMENTS

| 4,363,794 A | | 12/1982 | Ochiai et al. .................. 424/52 |
| 4,486,179 A | * | 12/1984 | Brauer et al. .................. 106/35 |
| 4,850,872 A | | 7/1989 | Goldman et al. ............ 433/215 |
| 4,885,156 A | | 12/1989 | Kotilainen et al. ........... 424/54 |
| 5,855,870 A | | 1/1999 | Fischer ......................... 424/49 |
| 5,861,167 A | | 1/1999 | Lindskog et al. ............ 424/423 |
| 5,885,551 A | | 3/1999 | Smetana et al. .............. 424/49 |
| 5,962,550 A | * | 10/1999 | Akahane et al. .............. 106/35 |
| 6,013,274 A | | 1/2000 | Chaykin ...................... 424/440 |
| 6,017,516 A | | 1/2000 | Mody et al. .................. 424/55 |

* cited by examiner

Primary Examiner—Kevin Shaver
Assistant Examiner—Melba Bumgarner
(74) Attorney, Agent, or Firm—Gifford, Krass, Groh, Sprinkle, Anderson & Citkowski, P.C.

(57) ABSTRACT

A dental bonding formulation provides a single application step in which a chelating agent present within the formulation is capable of complexing ions present in a dentinal tubule calcified deposit. The formulation has a pH of between 1.2 and 4 to promote complexation without inducing excessive dentin etch. A curable resin is also present in the formulation to seal the underlying dentin surface.

7 Claims, No Drawings

DENTAL BONDING FORMULATION COMPLEXING CALCIFIED DEPOSITS ASSOCIATED WITH A DENTINAL TUBULE OPENING

RELATED APPLICATION

This application claims priority of United States Provisional Patent Application 60/211,359 filed Jun. 13, 2000 and is incorporated herein by reference.

FIELD OF THE INVENTION

The present invention relates to a solution for opening dentinal tubules and conditioning exposed roots, more particularly, to a solution containing a chelating agent and an acid such that the acid enhances the activity of the chelating agent without inducing etching.

BACKGROUND OF THE INVENTION

Sensitivity and structural failure are often complications of dental restoration. Such complications are often associated with the failure to remove cellular debris prior to adhering a dental restoration. Traditionally, chemo-mechanical procedures have been used to remove cellular debris. Unfortunately, the use of an abrasive grit with irrigation affords little penetration within dentinal tubules and further causes considerable discomfort to tooth root or exposed tooth pulp. The cellular debris adhering to exposed dentinal tubules and root surfaces represents dentin fragments associated with mechanical removal, necrotized and bacterial debris as well as calcified deposits. The calcified deposits tend to block dentinal tubules thereby creating a recess for bacterial infection, as well as an unstable anchorage for the bonding of a dental restorative. Since chemo-mechanical removal of calcified deposits is largely ineffective and acid etching dissolves dentin and tooth pulp unnecessarily, there exists a need for a solution used in conjunction with dental restoration which is capable of removing tooth fragments, necrotized and bacterial debris as well as calcific deposits without inducing etching of the tooth structure.

SUMMARY OF THE INVENTION

A dental restoration solution for root or dentinal tubule treatment includes an orally compatible solvent containing a chelating agent present from one weight percent to saturation in the solvent, the solvent at a pH of between 1.2 and 4. The restoration solution optionally contains additives such as an antimicrobial, a thickener, a fluoride salt, a dye and/or a flavorant. A process for conditioning a dental root or opening a dentinal tubule includes the step of exposing a dental surface for from 10 to 120 seconds to such a dental restoration solution in order to condition a dental root or open a dentinal tubule absent etching of dentin. An inventive chelating agent is also operative in a dental bonding formulation also including a curable resin, the formulation having a pH of between 1.2 and 4. A commercial kit is detailed including a dental restoration solution including an orally compatible solvent, and a chelating agent present from 1 weight percent to saturation in the solvent where the solvent is at a pH of between 1.2 and 4. The kit also includes instructions for the use of the solution as a pretreatment for a curable resin dental bond.

DETAILED DESCRIPTION OF THE INVENTION

A solution according to the present invention includes a chelating agent capable of complexing those ions which are present in a calcified deposit associated with a dentinal tubule opening. Solvent according to the present invention is orally compatible and illustratively includes water, ethanol, acetone and mixtures thereof. Suitable chelating agents useful in the present invention illustratively include ethylenediaminetetraacetic acid (EDTA), diethylenetriaminepentaacetic acid (DTPA), nitrilotriacetic acid (NTA), iminodiacetic acid (IDA), iminotriacetic acid (ITA), ethylenediamine (En), N,N'-diethylenediamine (Den), diethylenetriamine (DTN), diethylenetetramine (Trien), triaminotriethylene amine, propylenediamine, glycolic acid, hydroxybutyric acid, salicylic acid, benzoic acid, mixtures thereof and other polydentate chelating agents which are compatible with the buccal cavity and active in binding divalent cations such as $Ca^{2+}$, $Mg^{2+}$, $Fe^{2+}$, and the like. Binding of calcium ions a preferred function of a chelating agent according to the present invention. Preferably, the chelating agent of the present invention contains carboxylate moieties. More preferably, the chelating agent is DTPA. A chelating agent of the present invention is dissolved in an aqueous solution in an amount of about 3% by weight to solution saturation at 20° C. Chelating agent solutions are typically between 5% and 80% of the solution saturation quantity of the chelating agent.

According to the present invention, a chelating agent and additional acid where necessary are dissolved together in water to form a solution having a pH of from about 1.2 to 4. Unlike conventional etching solutions which typically have a pH of about 1 or less and are characterized by dissolving mineralized dentin surface as well as collagen, the present invention does not appreciably etch mineralized material nor dissolve collagen during short duration exposure of a tooth to a solution according to the present invention. Typical exposure times associated with the present invention are from about 5 to 120 seconds. As used herein, etching is defined as the dissolution of dentin to a depth of greater than 9 microns per minute.

Suitable pH lowering acids useful in the present invention illustratively include ascorbic, acetic, propionic, formic, succinic, hydrochloric, sulfuric, nitric, phosphoric, orthophosphoric and citric. Preferably, the acid of the present invention yields a solution pH of between 1.2 and 4. More preferably, the solution pH is between 1.4 and 2.5. Most preferably, the solution pH is between 1.4 and 2.0.

Optional additives to the inventive solution include an anti-microbial agent, a fluoride salt, a thickener, a dye and a flavorant. In particular, a thickener is desired in embodiments of the instant invention where viscous adhesion to a dentin surface is required.

Suitable anti-microbials operative in the present invention illustratively include chlorhexidine, tetracycline, benzalkonium chloride, acetyl pyridinium and alkyl benzoates. Preferably, an anti-microbial is present in the present invention from about 0 to 10% total solution weight. More preferably, the anti-microbial is present from about 0.5 to 5 total weight percent. The preferred anti-microbial according to the present invention is chlorhexidine.

Fluoride salts operative in the present invention illustratively include sodium fluoride, potassium fluoride, lithium fluoride, cesium fluoride, zirconium fluoride, ammonium fluoride, mono and poly-fluorophosphates, and fluoride salts of organics illustratively including hexylamine hydrofluoride, laurylamine hydrofluoride, cetylamine hydrofluoride, glycineamine hydrofluoride, lysine hydrofluoride, and mixtures of two or more. A fluoride salt according to the present invention is present in a range from about 0 to 1% total solution weight. More preferably, fluoride is present from about 0.1 to 0.5 total weight percent. The inorganic fluoride salts are preferred for use herein.

An additional thickener is optionally included herein. A thickener according to the present invention illustratively includes glycerol, polyethylene glycol, polyacrylic acid, polyacrylate, carboxymethylcellulose (CMC), nitrocellulose, a salt thereof, and mixtures thereof. A thickener according to the present invention is present from 0 to 5 total weight percent. Preferably, a thickener is present from about 0.5 to 3 total weight percent. A thickener serves to retain an inventive solution at the point of application.

A dye is optionally present to identify a tooth region contacted with the inventive solution. The dye illustratively including vegetable dye, food dyes, and gentian violet. A dye is present from 0 to 5 total weight percent. More preferably, a dye is present from 0.5 to 2 total weight percent.

While a solution according to the present invention is typically dabbed or dropped onto a specific site on a tooth for a limited period of time, a flavorant is optionally included. A flavorant is preferably present in embodiments of the instant invention applied as an oral rinse. The flavorants illustratively include plant extracts and oils including clove, spearmint, mint, citrus; sorbitol, and saccharin. A flavorant according to the present invention being present from 0 to 5 total weight percent. More preferably, a flavorant being present from 1 to 3 total weight percent.

The present invention is also operative as an additive to a conventional curable dental resin or primer therefor. Thus, the instant invention is operative as a separate formulation or as an additive to a dental bonding primer and resin kit for use in a total etch bond technique such as Prompt®, L-Pop® (ESPE, Plymouth Meeting, PA) and Clearfill-SE® (J. Morita, Japan). A resin formulation according to the present invention affords a single application step in which the resin additive package removes the calcified smear layer and cures to seal the underlying dentin surface. Through control of the resin cure rate, the smear layer debris forms inclusions within a cured resin matrix. Resins illustratively operative herein include acrylates, polycarbonates, polyurethanes, and methacrylates such as bis-phenol A-, hydroxyalkyl-, alkylene glycols-, polyols-, and glycidyl derivatives thereof; 2,2'-bis [(3-methacryloxy-2-hydroxy propoxy)-phenol]-propane (bis-GMA); and 2-hydroxyethylene methacrylate (2-HEMA). Preferably, the chelating agent as part of a resin formulation is present from a 1 to 17 total weight percent of the resin formulation, with the resin. formulation having a pH of between 1.2 and 4.0. Preferably, the pH is between 1.4 and 2.5.

In order to facilitate storage of a resin formulation, it is preferred that the additive package including the chelating agent and acid be stored separately from the resin component. The two part system being mixed at the time of application. It is appreciated that a resin formulation in addition to the additive package upon mixing optionally includes filler, pigments, catalyst and adhesion promoter conventional to the art. The cure time for a resin formulation according to the present invention ranges from 30 seconds to about 5 minutes. The cure being exacted by a variety of free radical and acid condensation catalysts conventional to the art and determined by the identity of resin monomer or oligomers utilized.

The present invention is illustrated through the following specific examples. These examples are not intended to limit the scope of the present invention as defined by the appended claims.

EXAMPLE 1

4 ml of 17% by weight EDTA solution is mixed with 2 ml of freshly squeezed lemon juice and the pH adjusted to 1.4 with the addition of water. A drop of the inventive solution is applied to a freshly abraded dentin surface for 30 seconds. Immediately thereafter a HEMA (hydroxy ethyl methacrylate) solution is applied to the tooth region exposed to the inventive solution. A conventional resin filling is thereafter formed. A greater than 60% reduction in sensitivity is noted for fillings pretreated with the inventive solution one year later as compared to a control group not exposed to the inventive solution.

EXAMPLES 2–5

The following dental restoration solution formulations were prepared according to the present invention as detailed in Table 1.

The formulations of Examples 2–5 produced subjectively less sensitivity and complications within one year similar to those detailed in Example 1 as compared to a control group not exposed to the inventive solution.

EXAMPLE 6

5 grams of DTPA is dissolved in a liter of water acidified to pH 2.0 by acetic acid addition. The resulting solution is applied to a cadaver molar for 60 seconds. Scanning electron micrographs of the molar show opening of the dentinal tubules compared to a control from the same cadaver. No molar etching is observed.

While the present invention has been described in terms of certain preferred embodiments, it is appreciated that one skilled in the art will recognize many modifications and variations hereof that remain within the scope and spirit of the present invention. Such variations and modifications are considered to be within the scope of the present invention according to the appended claims.

TABLE 1

|  | 2 | Total wt % | 3 | Total wt % | 4 | Total wt % | 5 | Total wt % |
| --- | --- | --- | --- | --- | --- | --- | --- | --- |
| Chelating agent | EDTA | 15.0 | Trien | 5.0 | EDTA | 10.0 | NTA | 10.0 |
| Acid | acetic pH | 1.5 | citric | 1.8 | succinic |  | orthophosphoric |  |
| Anti-microbial | chlorhexidine | 2.0 | — |  | chlorhexidine | 0.5 | benzalkonium chloride | 5.0 |
| Thickener | — |  | CMC |  | nitrocellulose | 0.5 | CMC | 2.0 |
| Fluoride salt | — |  | NaF | 0.1 | hexylamine HF | 0.3 | — |  |
| Dye | — |  | gentian violet | 0.2 | green vegetable dye | 0.5 | green vegetable dye | 0.5 |
| Flavorant | — |  | spearmint oil | 2.0 | — |  | — |  |

What is claimed is:

1. A dental bonding formulation comprising:

a curable resin; and a chelating agent present in said formulation, said formulation having a pH of between 1.2 and 4, said chelating agent capable of complexing ions present in a dentinal tubule calcified deposit, and said formulation capable of curing to seal a dentin surface.

2. The dental bonding formulation of claim 1 further comprising an anti-microbial agent.

3. The dental bonding formulation of claim 1 wherein said chelating agent is selected from the group consisting of ethylenediaminetetraacetic acid (EDTA), diethylenetriaminepentaacetic acid (DTPA), nitrilotriacetic acid (NTA), iminodiacetic acid (IDA), iminotriacetic acid (ITA), ethylenediamine (En), N,N'-diethylenediamine (Den), diethylenetriamine (DTN), diethylenetetramine (Trien), triaminotriethylene amine, propylenediamine, glycolic acid, hydroxybutyric acid, salicylic acid, benzoic acid, mixtures thereof and other polydentate chelating agents which are compatible with the buccal cavity.

4. The dental bonding formulation of claim 1 wherein the chelating agent is EDTA.

5. The dental bonding formulation of claim 1 wherein the chelating agent is DTPA.

6. The dental bonding formulation of claim 1 wherein said curable resin is selected from the group consisting of: acrylates, polycarbonates, polyurethanes, and methacrylates.

7. The dental bonding formulation of claim 1 wherein said chelating agent is present from 1 to 17 total weight percent.

* * * * *